(12) United States Patent
Jain et al.

(10) Patent No.: US 8,936,900 B2
(45) Date of Patent: Jan. 20, 2015

(54) CALIXARENE AND PHOTORESIST COMPOSITION COMPRISING SAME

(71) Applicants: Rohm and Haas Electronic Materials LLC, Marlborough, MA (US); Dow Global Technologies LLC, Midland, MI (US)

(72) Inventors: Vipul Jain, Westborough, MA (US); D. Patrick Green, Midland, MI (US); James W. Thackeray, Braintree, MA (US); Brad C. Bailey, Midland, MI (US); Su Jin Kang, Grafton, MA (US)

(73) Assignees: Rohm and Haas Electronic Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 83 days.

(21) Appl. No.: 13/624,579

(22) Filed: Sep. 21, 2012

(65) Prior Publication Data

US 2013/0078569 A1 Mar. 28, 2013

Related U.S. Application Data

(60) Provisional application No. 61/538,670, filed on Sep. 23, 2011.

(51) Int. Cl.
*G03F 7/004* (2006.01)
*C07C 43/02* (2006.01)
*C07C 309/00* (2006.01)

(52) U.S. Cl.
USPC ........ 430/270.1; 430/322; 430/326; 430/942; 562/88; 568/632

(58) Field of Classification Search
USPC .............. 430/630, 631, 632, 270.1, 322, 326, 430/942; 562/88; 568/632
See application file for complete search history.

(56) References Cited

U.S. PATENT DOCUMENTS 6,093,517 A 7/2000 Ito et al.
6,803,171 B2 10/2004 Gronbeck et al.
(Continued)

FOREIGN PATENT DOCUMENTS

EP 1345080 A2 9/2003
EP 1767991 A2 3/2007
(Continued)

OTHER PUBLICATIONS

International Publication No. 2004036315 A1; Publication Date: Apr. 29, 2004; Abstract Only, 2 pages.
(Continued)

*Primary Examiner* — Amanda C. Walke
(74) *Attorney, Agent, or Firm* — Cantor Colburn LLP

(57) ABSTRACT

A molecular glass compound comprises a vinyl ether adduct of an aromatic vinyl ether of formula $C(R^1)_2=C(R^2)-O-(L)_n-Ar^1$, and a calix[4]arene, wherein $R^1$ and $R^2$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $Ar^1$ is a halo-containing monocyclic, or substituted or unsubstituted polycyclic or fused polycyclic $C_{6-20}$ aromatic-containing moiety, wherein $R^1$ and $R^2$ are connected to $Ar^1$ when either or both of $R^1$ and $R^2$ is a single bond and n is 0. A photoresist, comprising the molecular glass compound, a solvent, and a photoacid generator, a coated substrate, comprising (a) a substrate having one or more layers to be patterned on a surface thereof; and (b) a layer of a photoresist composition over the one or more layers to be patterned, and a method of forming the molecular glass compound, are also disclosed.

12 Claims, 1 Drawing Sheet

A B C

(56) References Cited

U.S. PATENT DOCUMENTS

| | | |
|---|---|---|
| 7,037,638 B1 | 5/2006 | Afzali-Ardakani et al. |
| 7,514,197 B2 | 4/2009 | Ochiai et al. |
| 7,642,145 B2 | 1/2010 | Fukuda et al. |
| 7,659,047 B2 | 2/2010 | Kojima et al. |
| 7,705,189 B2 | 4/2010 | Nishikubo et al. |
| 8,110,334 B2 * | 2/2012 | Echigo et al. ............ 430/270.1 |
| 2005/0026077 A1 * | 2/2005 | Gronbeck et al. ......... 430/270.1 |
| 2005/0271971 A1 | 12/2005 | Ueda et al. |
| 2007/0122734 A1 | 5/2007 | Roberts et al. |
| 2007/0224540 A1 | 9/2007 | Kamimura et al. |
| 2009/0081589 A1 | 3/2009 | Toukhy et al. |
| 2010/0136706 A1 * | 6/2010 | Miyata et al. ............... 436/148 |
| 2010/0239980 A1 | 9/2010 | Okuyama et al. |
| 2010/0266952 A1 | 10/2010 | Kashiwamura et al. |
| 2011/0020756 A1 * | 1/2011 | Bozano et al. ............... 430/326 |
| 2011/0197668 A1 * | 8/2011 | Miller et al. .................. 73/172 |
| 2012/0107749 A1 | 5/2012 | Tono et al. |
| 2012/0282546 A1 * | 11/2012 | Takasuka et al. .......... 430/281.1 |
| 2013/0157195 A1 * | 6/2013 | Green et al. ............... 430/281.1 |

FOREIGN PATENT DOCUMENTS

| | | |
|---|---|---|
| EP | 1830228 A1 | 9/2007 |
| EP | 1906241 A1 | 4/2008 |
| EP | 1906248 A1 | 4/2008 |
| EP | 2080750 A1 | 7/2009 |
| JP | 2008116677 A | 5/2008 |
| JP | 2009173625 A | 8/2009 |
| WO | 2004036315 A1 | 4/2004 |
| WO | 2005097725 A1 | 10/2005 |
| WO | 2006129574 A1 | 12/2006 |
| WO | 2009075307 A1 | 6/2009 |
| WO | 2009075308 A1 | 6/2009 |
| WO | 2009119784 A1 | 10/2009 |
| WO | 2009143357 A2 | 11/2009 |
| WO | 2010026973 A1 | 3/2010 |
| WO | 2010067627 A1 | 6/2010 |

OTHER PUBLICATIONS

International Publication No. 2005097725 A1; Publication Date: Oct. 20, 2005; Abstract Only, 2 pages.
International Publication No. 2006129574 A1; Publication Date: Dec. 7, 2006; Abstract Only, 2 pages.
Japanese Patent No. 2008116677 A; Publication Date: May 22, 2008; Abstract Only, 1 page.
International Publication No. 2009075307 A1; Publication Date: Jun. 18, 2009; Abstract Only, 2 pages.
International Publication No. 2009075308 A1; Publication Date: Jun. 18, 2009; Abstract Only, 2 pages.
International Publication No. 2009119784 A1; Publication Date: Oct. 1, 2009; Abstract Only, 2 pages.
Japanese Patent No. 2009173625 A; Publication Date: Aug. 6, 2009; Abstract Only, 2 pages.
International Publication No. 2010067627 A1; Publication Date: Jun. 17, 2010; Abstract Only, 1 page.
CN1938259 A; English Abstract; Date of Publication Mar. 28, 2007; 1 page.
TW200421026; English Abstract; Date of Publication Oct. 16, 2004; 1 page.
KR 20040045323 A; Machine Translation; Date of Publication: Jun. 1, 2004; 51 pages.
WO 2008136372 A1 with English Abstract; Date of Publication Nov. 13, 2008; 51 pages.

* cited by examiner

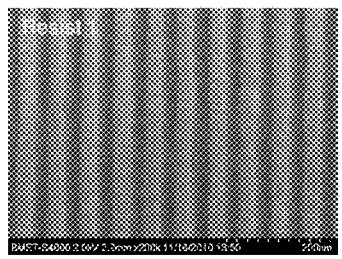 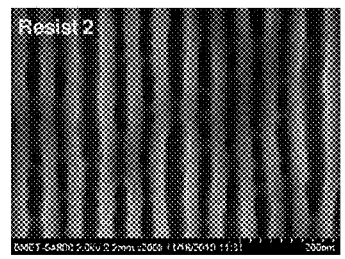 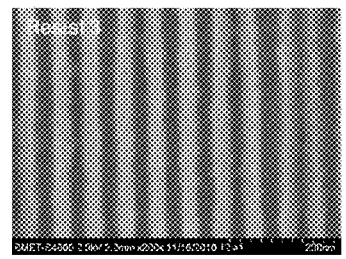
A  B  C

CALIXARENE AND PHOTORESIST COMPOSITION COMPRISING SAME

This application is a nonprovisional filing of and claims priority to provisional U.S. application No. 61/538,670, filed on Sep. 23, 2011, the contents of which are incorporated herein by reference in their entirety.

BACKGROUND

Design rules for advanced generation microlithography (i.e., beyond 193 nm immersion lithography and into next generation optics such as e-beam, X-ray, and extreme ultraviolet (EUV) lithography operating at a very short wavelength of 13.4 nm) are trending toward smaller and smaller dimensions, for example, 30 nm and below. In general, depth of focus (DOF) necessarily decreases with higher resolution due to the higher numerical aperture (NA) and therefore resist thickness also decreases to commensurate the smaller and smaller feature sizes. With narrower linewidths and thinner resist films, consistency issues such as line edge roughness (LER) and resolution take on increasing significance limiting the performance and usefulness of photoresists. These phenomena are of interest in the fabrication of semiconductor devices; for example, excessive LER can lead to poor etch and lack of linewidth control in, for example, transistor and gate architecture, potentially causing short circuits and signal delay. Since the radius of gyration of polymeric materials generally used to prepare EUV photoresists is essentially larger than the LER requirement (i.e., less than 3 nm), small, discrete and well defined molecules which when cast form amorphous films, and commonly known as molecular glasses, have been considered as possible candidates for developing EUV photoresist platforms.

Molecular glasses have been used in negative and positive tone resists. U.S. Patent Application Publication No. 2010/0266952 A1 describes the use of calix[4]arenes prepared from resorcinol/pyrogallol and an aldehyde having a carboxylate group, and having dissolution control groups attached to the hydroxy groups of the resorcinol/pyrogallol. However, there remains a need for calix[4]arene based photoresists which have improved resolution to meet the stringent requirements for photoresists having desirably high resolution and low LER.

STATEMENT OF INVENTION

One or more of the above and other deficiencies of the prior art may be overcome by a molecular glass in accordance with the invention, comprising a vinyl ether adduct of an aromatic vinyl ether of formula $C(R^1)_2 = C(R^2) - O - (L)_n - Ar^1$, and a calix[4]arene, wherein $R^1$ and $R^2$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $Ar^1$ is a halo-containing monocyclic, or substituted or unsubstituted polycyclic or fused polycyclic $C_{6-20}$ aromatic-containing moiety, wherein $R^1$ and $R^2$ are connected to $Ar^1$ when either or both of $R^1$ and $R^2$ is a single bond and n is 0.

A photoresist also comprises the molecular glass compound, a solvent, and a photoacid generator.

A coated substrate comprises (a) a substrate having one or more layers to be patterned on a surface thereof; and (b) a layer of a photoresist composition over the one or more layers to be patterned.

A method of forming a molecular glass compound comprises combining a calix[4]arene, and an aromatic vinyl ether of formula $C(R^1)_2 = C(R^2) - O - (L)_n - Ar^1$, wherein $R^1$ and $R^2$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $Ar^1$ is a halo-containing monocyclic, or substituted or unsubstituted polycyclic or fused polycyclic $C_{6-20}$ aromatic-containing moiety, wherein $R^1$ and $R^2$ are connected to $Ar^1$ when either or both of $R^1$ and $R^2$ is a single bond and n is 0; in the presence of an acidic catalyst.

A method of forming a patterned substrate comprises exposing the coated substrate to activating radiation.

BRIEF DESCRIPTION OF THE DRAWINGS

The foregoing and other objects, features, and advantages of the invention are apparent from the following detailed description taken in conjunction with the accompanying drawings in which:

The FIGURE shows 1:1 line/space scanning electron micrograph (SEM) images of exemplary photoresists (A and B) and a comparative resist (C).

DETAILED DESCRIPTION

Disclosed herein is a molecular glass compound useful for preparing photoresists. The molecular glass compounds are tetrameric calix[4]arenes having free hydroxy groups modified using acetal chemistry to include base-stable but acid-cleavable aromatic protecting groups.

Calix[4]arenes are discrete cyclic tetrameric compounds having an alternating structure derived from the reaction of a phenolic compound with an aldehyde. The core structure is preferably bowl-shaped tetrameric calix[4]arene formed from aromatic compounds having hydroxy groups and aldehydes preferably also having hydroxy groups, where some or all of the hydroxyl groups are reacted with aromatic vinyl ethers to form the adduct which is an acetal protection group. As used herein, "adduct" refers to the addition product of the vinyl ether with an aromatic hydroxy group unless otherwise specified. Calix[4]arenes exist in four different conformers: cis-cis-cis, cis-trans-cis, cis-cis-trans, and trans-trans-trans. Typically, the thermodynamically most favored conformer is the cis-cis-cis in which all four arene rings are flipped in the same direction such that the calix[4]arene molecule possesses a C4 symmetry axis, in contrast to the trans-trans-trans isomer which possesses a C2 symmetry axis. When prepared using hydroxyaromatic compounds such as resorcinol (1,3-dihydroxy benzene) for example, the hydroxy groups effectively lock the conformation by geometrically-favored hydrogen-bonding interactions between hydroxy groups on adjacent aromatic rings. This locked conformation imparts a "bowl-shaped" structure to the all-cis calix[4]arene.

The presence of the acetal groups derived from aromatic vinyl ethers on the calix[4]arene imparts dissolution inhibition in alkaline developers, which upon exposure to acid, are cleaved to enhance dissolution and contrast of the calix[4]arene, as well as increased glass transition temperature. Upon exposure of a coated film of photoresist prepared using the protected calix[4]arene and a photoacid generator, acid hydrolysis of the acetal protecting group renders the core soluble in alkaline developer.

The molecular glass compound thus includes a vinyl ether adduct of an aromatic vinyl ether of formula (I):

$$C(R^1)_2 = C(R^2) - O - (L)_n - Ar^1 \qquad (I)$$

and a calix[4]arene. In formula (I), $R^1$ and $R^2$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $Ar^1$ is a halo-containing monocyclic, or substituted or unsubstituted polycyclic or fused polycyclic $C_{6-20}$ aromatic-containing moiety. $R^1$ and $R^2$ can be, for example, hydrogen to form an unsubstituted vinyl group, or can be connected to $Ar^1$ when either or both of $R^1$ and $R^2$ is a single bond and n is 0, to form an endocyclic vinyl ether. As used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. "Halosubstituted" means that the group specifically includes a halogen substituent (i.e., F, Cl, Br, I), and may include these halogens alone, or in combination with other substituents listed above. It will be understood that any group or structure disclosed with respect to the formulas herein may be so substituted unless otherwise specified, or where such substitution would significantly adversely affect the desired properties of the resulting structure. Also as used herein, the prefix "halo-" means that the group includes any halogen or combination thereof (F, Cl, Br, I).

Preferably, the aromatic vinyl ether is of formula:

 (II)

wherein L is a $C_{1-10}$ linking group, n is 0 or 1, and $Ar^2$ is a $C_{6-20}$ aryl, $C_{6-20}$ heteroaryl, $C_{6-20}$ haloaryl, $C_{7-20}$ aralkyl, $C_{7-20}$ heteroaralkyl, or $C_{7-20}$ haloaralkyl. Also as used herein, the prefix "hetero-" means any non-carbon, non-halogen atom. Preferred heteroatoms include B, N, P, O, S, and Si. Preferably, in formulas (I) and (II), L is $—((—CH_2)_m—O—)_p—$, or $—((—CH_2—)_m—O)_p—C(O)—$, wherein m and p are each independently an integer of 0 to 10. Preferably, a shorter linking group L can be used, where m and/or p is 0 or 1.

Exemplary aromatic vinyl ethers include those having the following formulas:

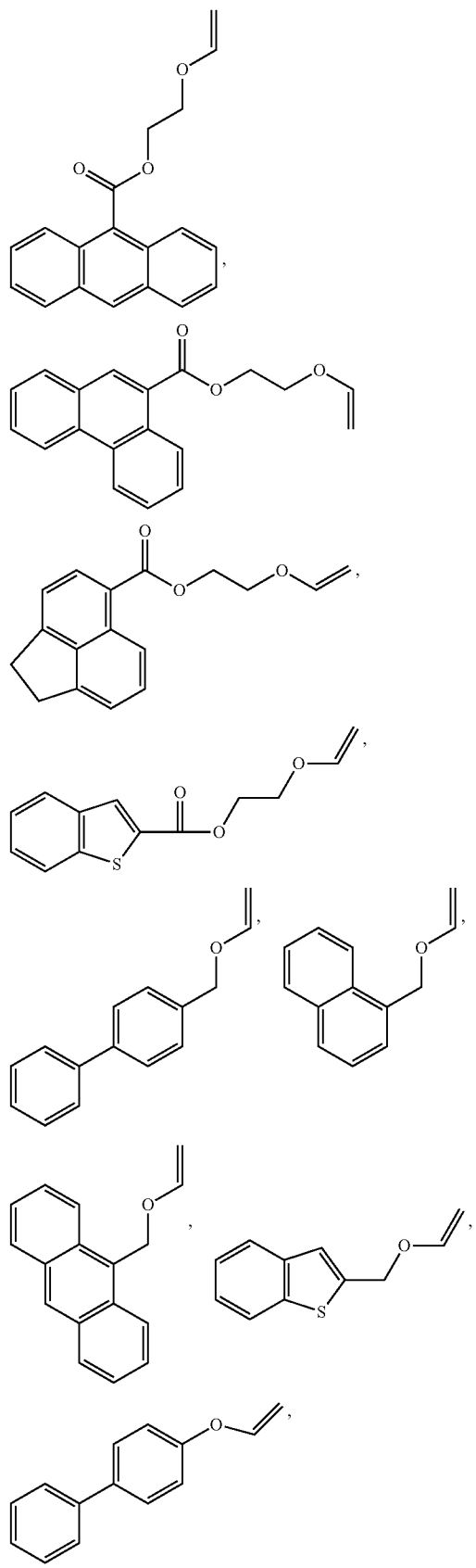

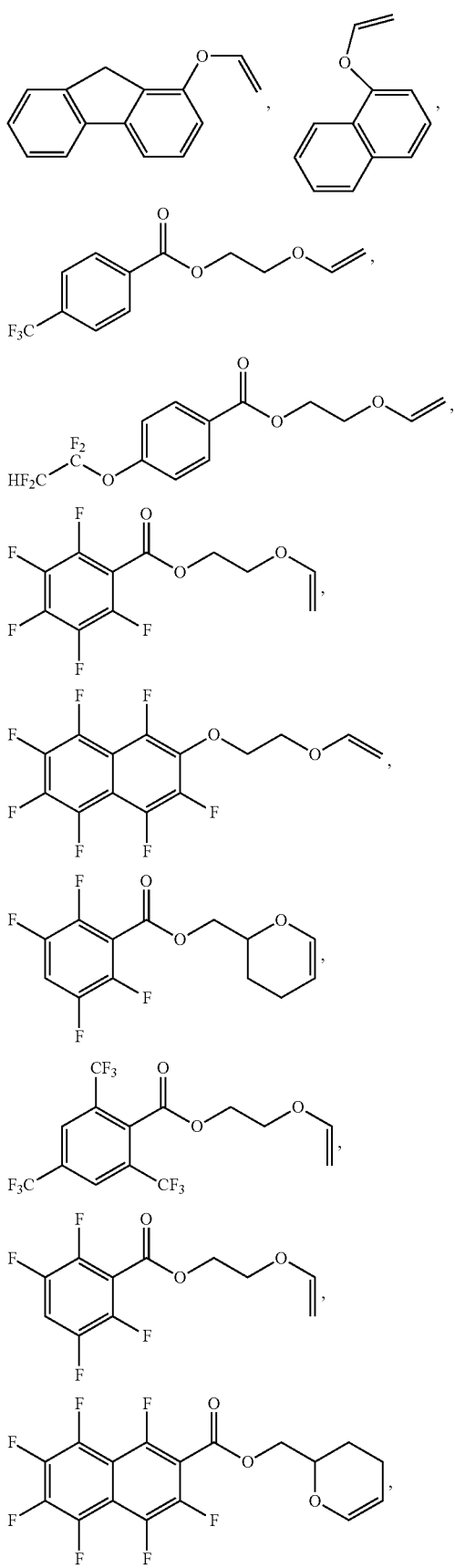

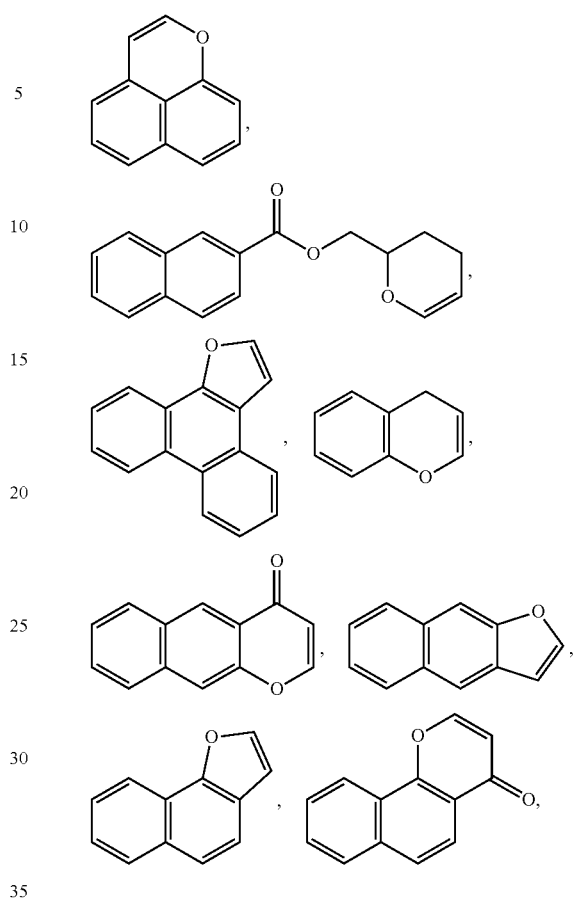

or a combination comprising at least one of the foregoing.

Combinations of vinyl ethers can thus also be used. For example, two or more different aromatic vinyl ethers can be reacted with the calix[4]arene to form the adduct. Alternatively, combinations of the aromatic vinyl ether and an aliphatic vinyl ether can be used. Preferably, where a combination of aliphatic and aromatic vinyl ethers are used, the vinyl ether adduct further includes a cycloaliphatic vinyl ether of the formula (III):

wherein $R^3$ and $R^4$ are each independently H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $R^5$ is substituted or unsubstituted and is a $C_{2-30}$ alkyl or $C_{2-40}$ haloalkyl.

Exemplary cycloaliphatic vinyl ethers include cycloalkyls and those based on carbon cage structure such as adamantane and norbornane:

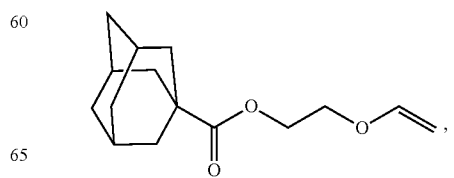

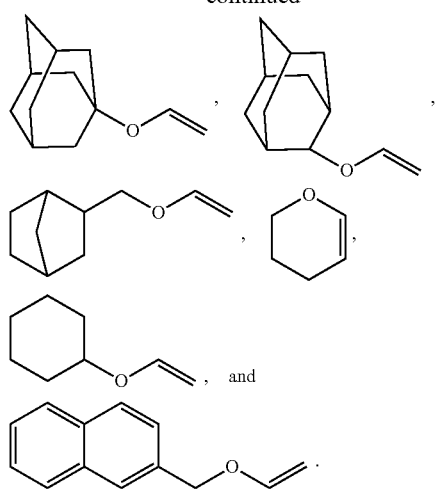
Further exemplary aromatic vinyl ethers include those of general structure:
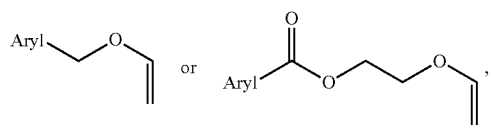
wherein Aryl is, for example, an aromatic moiety having one of the following structures:
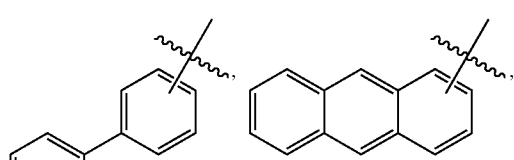
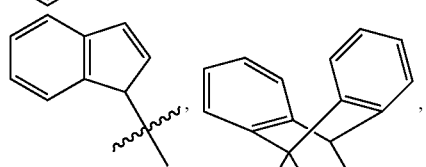
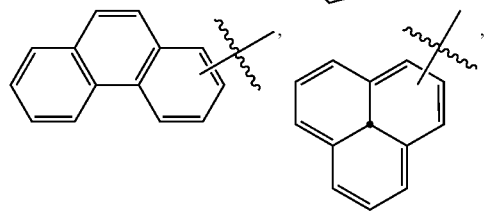
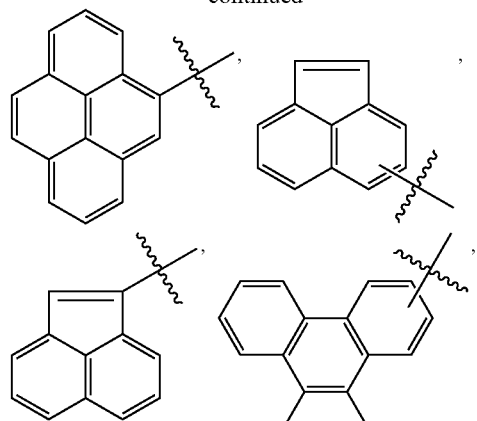
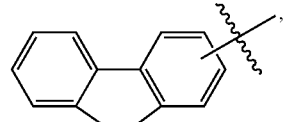
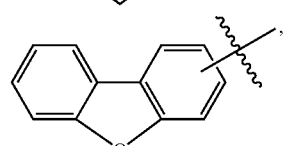
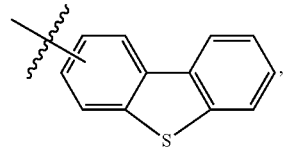
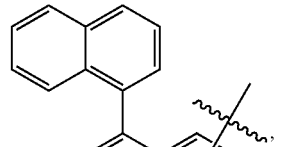
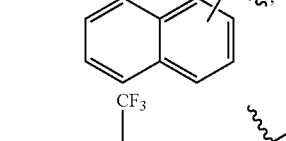
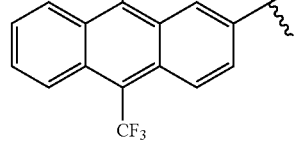
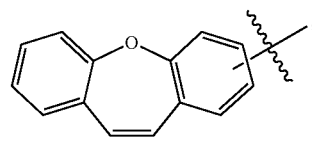
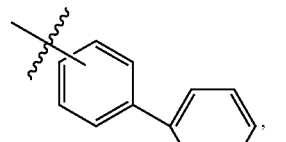

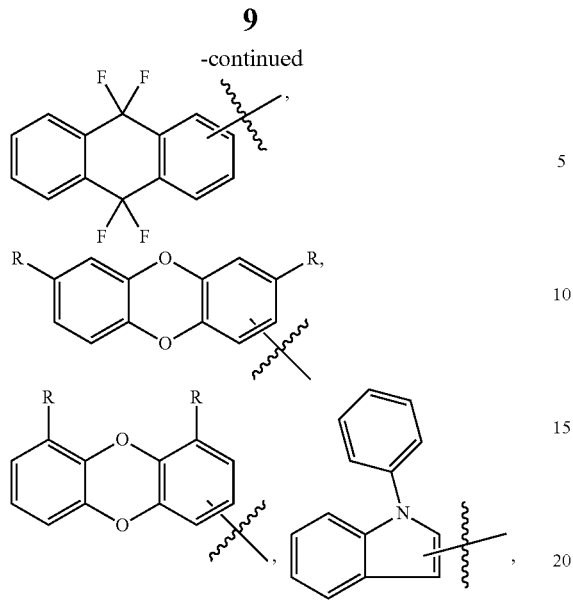

or a combination comprising at least one of the foregoing.

The calix[4]arene itself preferably comprises the tetrameric reaction product of an aromatic compound of formula (IV):

$$C_6R^6_x(OR^7)_y \qquad (IV)$$

wherein $R^6$ is H, F, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, $R^7$ is H, $C_{1-20}$ alkyl, $C_{1-20}$ haloalkyl, x is 6−y and y is 2 or 3, and at least two $OR^7$ groups are meta to one another, and an aldehyde. Exemplary aromatic compounds include resorcinol, pyrogallol, 3-methoxyphenol, or 3-ethoxyphenol.

The aldehyde is preferably of formula (V):

$$R^8\text{—CHO} \qquad (V)$$

wherein $R^8$ is substituted or unsubstituted and is $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl. Exemplary aldehydes include benzaldehyde, 4-hydroxybenzaldehyde, 2,4-dihydroxybenzaldehyde, 2-hydroxy-4-methoxy benzaldehyde, 3-methoxy-4-hydroxybenzaldehyde, 3-ethoxy-4-hydroxybenzaldehyde, or 3,5-dimethyl-4-hydroxybenzaldehyde.

Exemplary calix[4]arenes thus include the following structures:

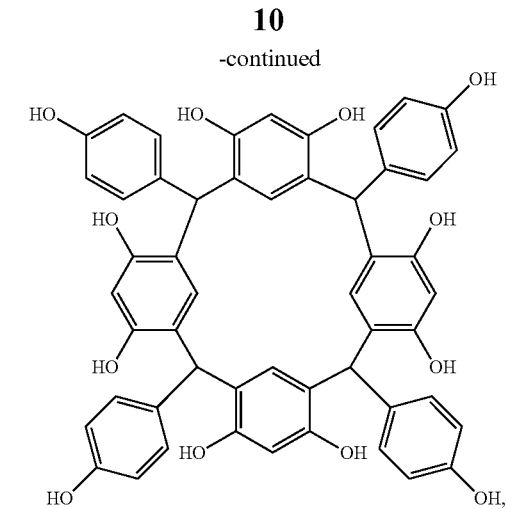

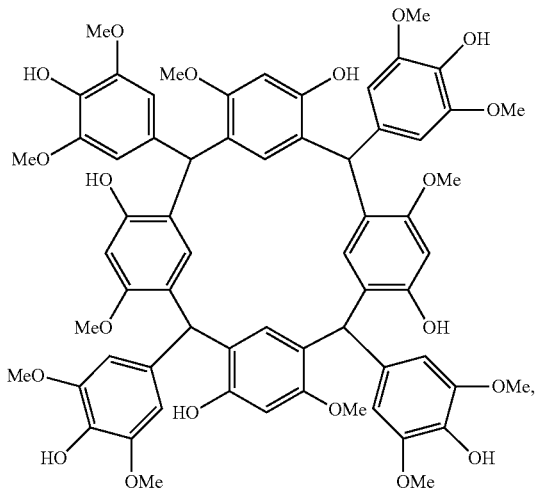

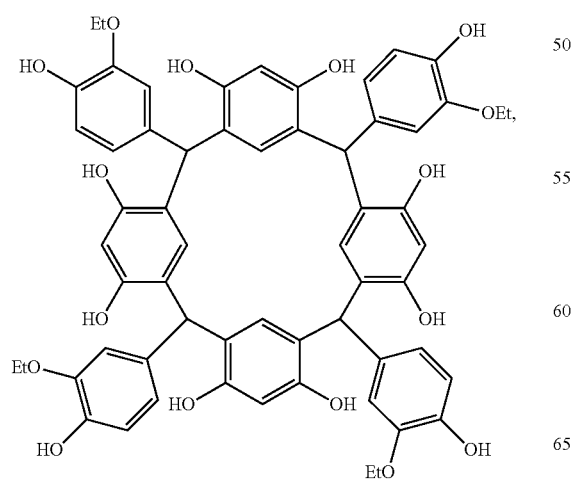

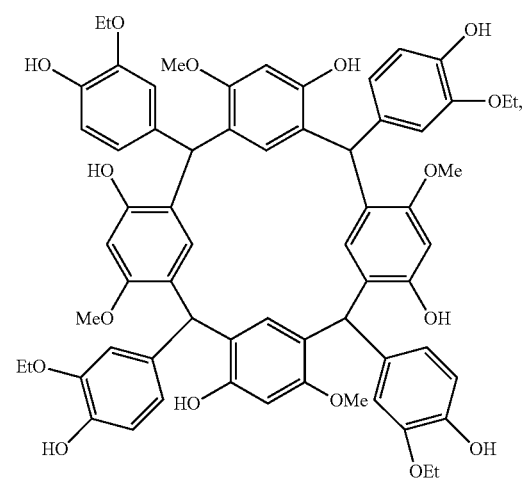

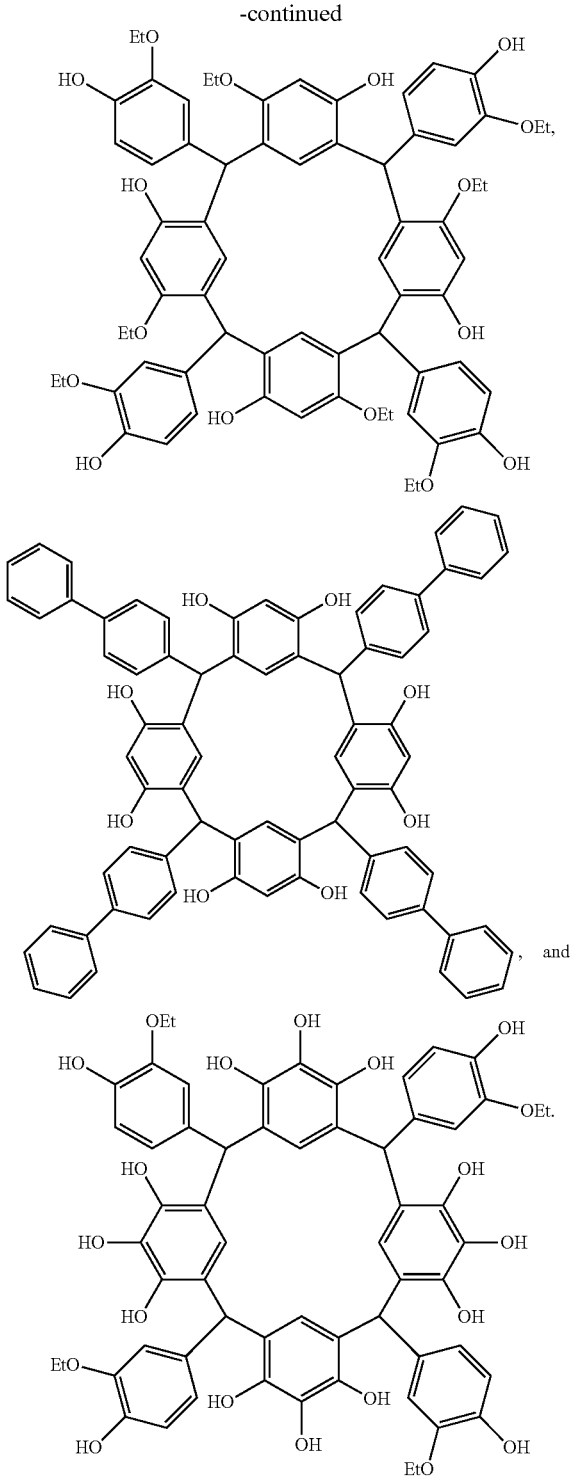

, and

Calix[4]arenes thus preferably include 4 or more hydroxy groups per molecule, more preferably 4 to 12 hydroxy groups, where during reaction to form the adduct a statistical distribution of the aromatic vinyl ether groups, or aromatic and aliphatic groups, form on each core molecule. It will thus be appreciated that the adduct represents an average structure based on the stoichiometry of the aromatic or aromatic and aliphatic vinyl ethers used, and the available reactive hydroxy groups present on the calix[4]arene core.

The calix[4]arene is the condensation reaction product of the above aromatic compound and aldehyde or derivative thereof, carried out in acidified polar solvent, such as aqueous acidic solution, an acidified alcohol-water mixture, or an acidified alcohol mixture. Suitable solvents and solvent mixtures for carrying out the condensation include, but are not limited to, hydrochloric acid in water, methanol, ethanol, propanol, ethylene glycol, propylene glycol, ethylene glycol methyl ether, propylene glycol methyl ether, and combinations of the foregoing alcohols with water. Preferably, the solvent system is selected such that the cis-cis-cis isomer of the calix[4]arene precipitates preferentially. The condensation may be carried out at a temperature greater than about 70° C., more preferably greater than about 80° C. The calix[4]arene can be recovered as a precipitate, where the thermodynamic product (the cis-cis-cis isomer) can have lower solubility in aqueous solvents and can thus be isolated as a precipitate.

The condensation may be carried out in batch mode, by batch addition of monomers and acid catalyst to the reaction, by metered addition of separate feeds of one or more of the components (aromatic compound and aldehyde) to the reaction mixture, or any other suitable method for combining the reactants. As disclosed herein, the calix[4]arenes are discrete molecules and are not polymeric, and have a homogeneous composition, being the condensation product of a single aromatic compound with a single aldehyde; though it will be appreciated that while a polymeric intermediate (a condensation homopolymer) is initially formed, the calix[4]arene is the thermodynamic product of both oligomerization to directly obtain the calix[4]arene, and chain scission and end-group recombination of tetrameric segments of any intermediate polymer or thermodynamically disfavored conformer (i.e., cis-cis-trans, cis-trans-cis, trans-trans-trans).

The calix[4]arenes may have a molecular weight of less than or equal to 2,000 g/mol, preferably less than or equal to 1,500 g/mol. It will be appreciated that due to the nature of the condensed tetrameric product, the calix[4]arene core itself has a discrete and defined stoichiometry and hence has a theoretical polydispersity of 1. Molecular weights may be determined for the discrete compounds using mass spectrometry using for example field-desorption mass spectrometry, laser ablation mass spectrometry, or other methods suitable for obtaining the molecular weight of the calix[4]arene and adducts.

The adduct is the further condensation product of the aromatic vinyl ether with the calix[4]arene.

The adduct of the calix[4]arene with the aromatic vinyl ether may be prepared by the reaction of the vinyl ether with the hydroxy group on the calix[4]arene. For example, the calix[4]arene from the condensation of resorcinol and 3-ethoxy-4-hydroxybenzaldehyde may be treated with a vinyl ether such as, for example, 2-(2-vinyloxy)ethyl naphthalene-2-carboxylate (NCVE), alone or in combination with 2-(2-vinyloxy)ethyl adamantanecarboxylate, in the presence of a catalytic amount of acid (e.g., trifluoroacetic acid) and low moisture content (<0.1% w/w) in a solvent including ethers such as tetrahydrofuran, dioxane, 1,3-dioxolane or 1-methoxy-2-propyl acetate. The aromatic vinyl ether adduct of the calix[4]arene (i.e., the molecular glass compound) may be used as a solution in a suitable solvent useful in preparing photoresist compositions, or may be isolated as a solid by precipitation or spray-drying.

A photoresist is prepared from the molecular glass compound. The photoresist includes, in addition to the molecular glass compound, a solvent, and a photoacid generator.

Solvents include those suitable for use in photoresists. Exemplary solvents include anisole, alcohols including 1-methoxy-2-propanol, and 1-ethoxy-2 propanol, esters including ethyl lactate, n-butylacetate, 1-methoxy-2-propyl acetate, methoxyethoxypropionate, methyl hydroxy isobutyrate, ethoxyethoxypropionate, ketones including cyclohexanone and 2-heptanone, and a combination comprising at least one of the foregoing solvents.

Photoacid generators include generally those photoacid generators suitable for the purpose of preparing photoresists. Photoacid generators include, for example, an onium salt such as a mono- or diaryl iodonium or a mono-, di- or triaryl sulfonium salt, nitrobenzyl ester, sulfonic acid esters, diazomethane derivatives, glyoxime derivatives, sulfonic acid ester derivatives of an N-hydroxyimide compound and halogen-containing triazine compounds, or a combination comprising at least one of the foregoing, where the anion of the salt is a fluorinated or non fluorinated $C_{1-40}$ sulfonic acid or sulfonimide anion.

Other components that may be included in the photoresist include a photo-destroyable base, a quencher, and/or a surfactant.

Photo-destroyable bases include photo-decomposable cations, and preferably those useful for preparing PAGs, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids. Exemplary photo-destroyable bases include those combining cations and anions of the following structures where the cation is triphenylsulfonium or one of the following:

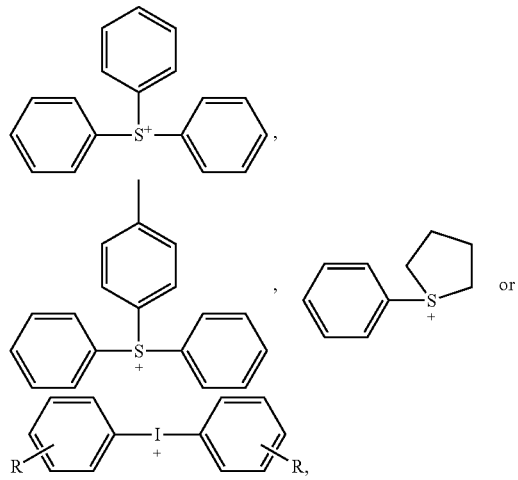

where R is independently H, a $C_{1-20}$ alkyl, a $C_{6-20}$ aryl, or a $C_{6-20}$ alkyl aryl, and the anion is

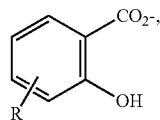

$RC(=O)—O^-$, or $^-OH$,
where R is independently H, a $C_{1-20}$ alkyl, a $C_{1-20}$ alkoxy, a $C_{6-20}$ aryl, or a $C_{6-20}$ alkyl aryl. Other photo-destroyable bases include those based on non-ionic photo-decomposing chromophores such as, for example, 2-nitrobenzyl groups and benzoin groups.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

Alternatively, or in addition, other additives may include quenchers that are non-photo-destroyable bases, such as, for example, those based on hydroxides, carboxylates, amines, imines and amides. Preferably, such quenchers include $C_{1-30}$ organic amines, imines or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicyclo undecene (DBU) or diazabicyclononene (DBM), or ionic quenchers including quaternary alkyl ammonium salts such as tetrabutylammonium hydroxide (TBAH), tetramethylammonium 2-hydroxybenzoic acid (TMA OHBA), or tetrabutyl ammonium lactate. Other additives including dissolution rate inhibitors and sensitizers commonly used in the art may also be included in the photoresist.

The photoresist composition disclosed herein may include the molecular glass compound in an amount of 50 to 99 wt %, preferably 55 to 95 wt %, more preferably 60 to 90 wt %, and still more preferably 65 to 90 wt % based on the total weight of solids. It will be understood that "molecular glass compound" used in this context of a component in a photoresist may mean only the molecular glass compounds disclosed herein, or a combination of the molecular glass compound with another molecular glass compound or polymer useful in a photoresist. The photoacid generator may be included in an amount of 0.1 to 50 wt %, preferably 0.5 to 40 wt %, more preferably 1 to 20 wt %, and still more preferably 2 to 15 wt % based on the total weight of solids. Where used, the photo-destroyable base may be included at of 0.01 to 5 wt %, preferably 0.1 to 4 wt %, and still more preferably 0.2 to 3 wt %, based on the total weight of solids. A surfactant may be included in an amount of 0.01 to 5 wt %, preferably 0.1 to 4 wt %, and still more preferably 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, preferably less than or equal to 20%, or more preferably less than or equal to 10%, based on the total weight of solids. The total solids content for the photoresist composition may be 0.01 to 50 wt %, preferably 0.1 to 40 wt %, more preferably 0.5 to 30 wt %, and still more preferably 1 to 20 wt %, based on the total weight of solids and solvent. It will be understood that the solids includes molecular glass and any associated polymer, photoacid generator, and any optional photo-destroyable base, quencher, surfactant, and additives, exclusive of solvent. It will be further understood that photoresist solids will be selected to provide the desired film thickness and so the total solids in solution is application-specific and should not be considered as limited to these solids contents.

The photoresist composition may be cast to form a layer on a substrate. Preferably, a photoresist layer thus comprises the molecular glass compound and photoacid generator after removal of solvent, and any additives such as photo-destroyable base and surfactant contacted to the surface of the substrate. Substrates may be any dimension and shape, and are preferably those useful for photolithography, such as silicon, silicon dioxide, strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, 40 cm, or larger in diameter, or other dimensions useful for wafer fabrication production.

Further, a method of forming an electronic device includes (a) applying a layer of a photoresist composition including the molecular glass compound on a surface of the substrate; and (b) patternwise exposing the photoresist composition layer to activating radiation. The method further includes (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 700 to 2,500 rpm. The coated wafer is spun to remove solvent, and is generally baked on a hot plate in a post-apply bake (PAB), also referred to in the art as a "soft bake," to further remove residual solvent and to remove free volume from the film to make it uniformly dense. Preferably, applying thus further includes a post-apply bake. A post-apply bake can be carried out at any suitable temperature. For example, a PAB can be carried out at less than or equal to about 120° C., preferably less than or equal to 110° C., and more preferably less than or equal to 100° C. A post-apply bake can be carried out for any suitable time, such as for example, less than or equal to about 120 seconds, preferably less than or equal to 110 seconds, and more preferably less than or equal to 100 seconds.

Patternwise exposure is then carried out using an exposure tool such as a stepper, in which the film is irradiated through a pattern mask and thereby is exposed patternwise. The method preferably uses advanced exposure tools generating activating radiation at wavelengths capable of high resolution. Thus, exposure is preferably carried out using e-beam radiation or extreme-ultraviolet (EUV) radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

After exposing, deblocking and/or catalyzing of a cross-linking reaction is further effected by performing a post-exposure bake (PEB), to diffuse the acid generated during exposing. A post-exposure bake can be carried out at any suitable temperature. For example, a PEB can be carried out at less than or equal to about 150° C., preferably less than or equal to 140° C., and more preferably less than or equal to 130° C. A post-exposure bake can be carried out for any suitable time, such as for example, less than or equal to about 120 seconds, preferably less than or equal to 110 seconds, and more preferably less than or equal to 100 seconds.

Developing the exposed photoresist layer is then accomplished by treating the exposed layer with a suitable developer capable of selectively removing the exposed portions of the film (where the photoresist is positive tone) or removing the unexposed portions of the film (where the photoresist is negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. The pattern is formed after developing. Since a PEB step is performed, do we need to mention it separately or is it a part of developing step.

The photoresist may be used to fabricate electronic and optoelectronic devices such as memory devices, processor chips (CPU's), graphics chips, and other such devices.

The invention is further illustrated by the following examples. All compounds used herein are available commercially except where a procedure is provided below. Structural characterization was carried out by nuclear magnetic resonance (NMR) spectrometry on an INOVA 400 or 500 NMR Spectrometer with OMNI-PROBE (operating at 400 or 500 MHz for proton, respectively) or a GEMINI 300 NMR Spectrometer (operating at 282 MHz for fluorine), each from Varian. Molecular weights for the molecular glasses were determined using a waters e2695 LC/3100 Mass Detector, manufactured by Waters Associates, running a reversed phase liquid chromatograph running a $C_{18}$ column, gradient elution with an acetonitrile/water, 80/20 to 100/0 (v/v) gradient at a flow of 0.5 mL/min) with a high resolution mass spectrometer detector (LC-MS) to provide m/z. Glass transition temperature (Tg) was determined using a DSC Q2000 Differential Scanning calorimeter, manufactured by TA Instrument Inc., operating at a ramp rate of 10° C./min. Unless otherwise specified, all reagents were obtained commercially.

The PAGs 4-hydroxyphenyldiphenylsulfonium cyclo(1,3-perfluoropropanedisulfonyl)imide salt, and 4-vinyloxyethoxyphenyldiphenylsulfonium cyclo(1,3-perfluoropropanedisulfonyl)imide salt (TPSVE Cy6, were obtained commercially from Toyo Gosei Co.

Several calix[4]arene cores were synthesized to contain different numbers of free hydroxy groups. The procedures are provided hereinbelow.

Calixarene 1 (C-4-hydroxy-3-ethoxyphenyl-calix[4]-3-ethoxy-phenolarene) was prepared according to the following procedure.

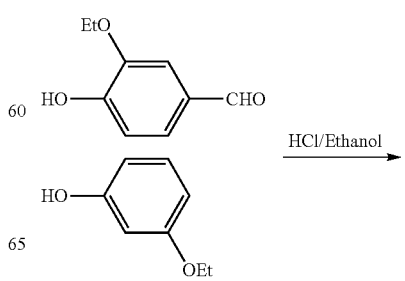

-continued

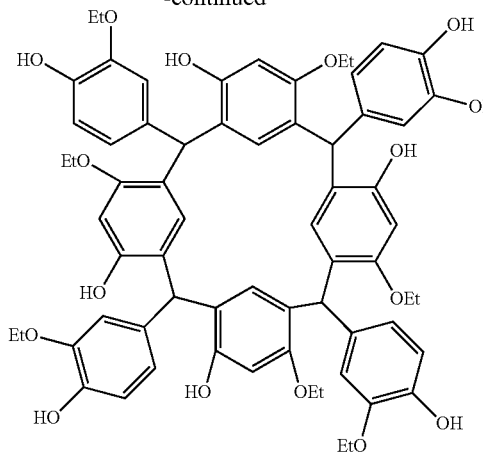
5

To a flask was added 3-ethoxyphenol (20.0 g, 141.8 mmol), concentrated HCl (10 ml), and ethanol (150 ml), and the resultant mixture was stirred at room temperature for 10 minutes. 3-Ethoxy-4-hydroxy benzaldehyde (23.8 g, 141.8 mmol), previously dissolved in 50 ml ethanol, was added dropwise to the mixture over a 10 minute period, and heated to reflux for 12 hours. The reaction mixture was then allowed to cool to room temperature, and the solid which precipitated from the cooled solution was collected by vacuum filtration. The crude product was then washed (3×100 mL) with water and cold methanol three times, recrystallized from methanol and the purified material collected and dried in vacuo at 70° C. to yield 10 g of white solid product (25%). $^1$H NMR (400 MHz, DMSO-$d_6$, TMSi): ppm 8.3-8.6 (m, phenoxy 4H), 7.7-8.0 (m, phenoxy 4H), 5.9-6.4 (m, aromatic 20H), 5.4-5.5 (m, benzylic 4H), 3.4-4.0 (m, methylenes 16H), 1.0-1.4 (m, CH$_3$ 24H). Mass Spectrum: m/z 1145.85.

Calixarenes 2 (C-4-hydroxy-3-ethoxyphenyl-calix[4]-3-methoxy-phenolarene) and 3 (C-4-hydroxy-3,5-dimethoxy-phenyl-calix[4]-3-methoxy-phenolarene) were also prepared according to the above procedure, except that for the calixarene of formula 2, 2-hydroxyanisole and 3-ethoxy-4-hydroxy benzaldehyde were used, and for the calixarene of formula 3, 2-hydroxyanisole and 3,5-dimethoxy-4-hydroxy-benzaldehyde were used. The structures of the calixarenes of formulas 1, 2, and 3 are shown below.

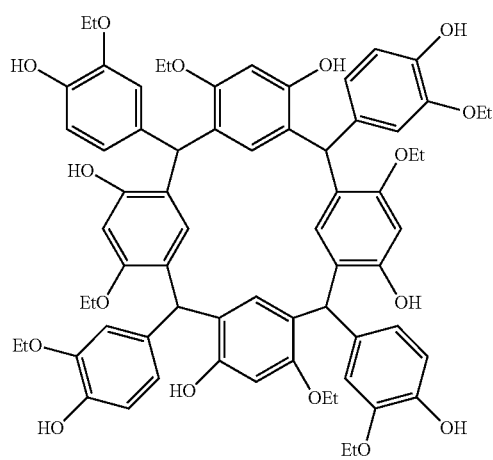
1

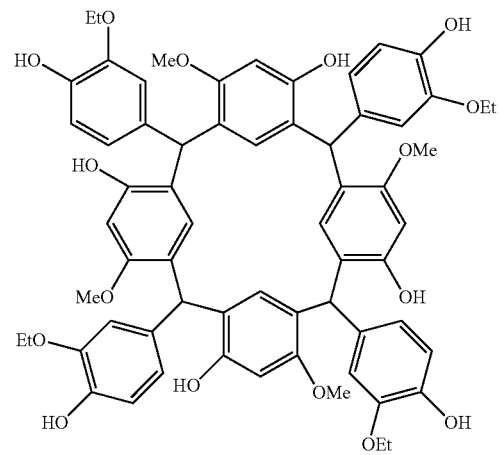
2

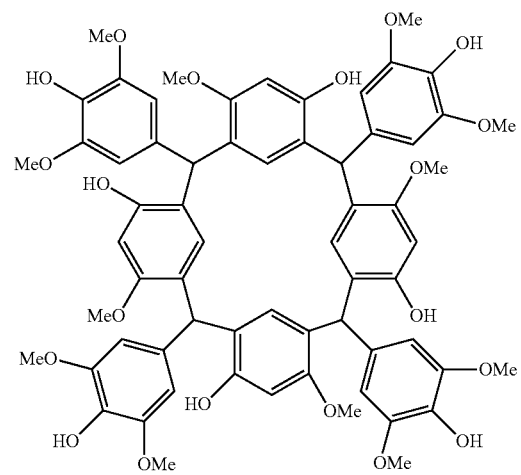
3

The analytical data for the calixarenes cores is listed in Table 1, below.

TABLE 1

| Calixarene core | Starting aldehyde | Starting 1,3-phenol | MS m/z |
| --- | --- | --- | --- |
| Calixarene 1 | 3-ethoxy-4-hydroxy benzaldehyde | 3-ethoxyphenol | 1145.85 g/mol |
| Calixarene 2 | 3-ethoxy-4-hydroxy benzaldehyde | 3-hydroxy anisole | 1089.18 g/mol |
| Calixarene 3 | 3,5-dimethoxy-4-hydroxybenzaldehyde | 3-hydroxy anisole | 1153.18 g/mol |

The vinyl ether adducts of calixarenes 1, 2, and 3 were then formed by the reaction of these calix[4]arenes with Naphthoylethyl vinyl ether (2-naphthylcarboxylic acid (also referred to as 2-naphthoic acid), 2-ethyl vinyl ether ester, abbreviated NCVE) (below).

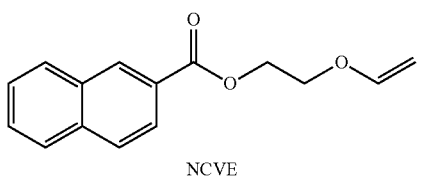 [SMILES: C=COCCOC(=O)c1ccc2ccccc2c1]

NCVE

Naphthoylethyl vinyl ether (NCVE) was prepared according to the following procedure. In a 300 mL three necked oven dried round bottom flask equipped with a magnetic stirrer, 25 g (0.145 mol) of 2-naphthoic acid and 24.07 g (0.17 mol) of potassium carbonate ($K_2CO_3$) were suspended in 100 ml of dioxane and the mixture stirred at room temperature for 1 hour, forming a thick slurry. 18.53 g (0.17 mol) of 2-chloroethylvinyl ether dissolved in 10 ml of dioxane was slowly added to the reaction mixture using a dropping funnel over a period of 1 hour and the reaction refluxed overnight for another 12 hours until a complete reaction was ascertained by thin layer chromatography (TLC) analysis (silica plates; eluant 1% (v/v) methanol in chloroform). The reaction was quenched by pouring the mixture slowly into 400 ml of 0.01% (v/v) hydrochloric acid (HCl) solution, the crude product was extracted into 300 ml of ethyl acetate, and the ethyl acetate extract was washed sequentially with water and brine to neutral pH. The ethyl acetate extracts were then dried over sodium sulfate, filtered and concentrated by rotary evaporation to afford 32 g (92% yield) of an amber oil which solidifies upon standing. The product was used without further purification. $^1$H NMR (500 MHz, Acetone-$d_6$): δ 8.64 (s, 1H), 8.08 (d, 2H, 8 Hz), 7.89 (d, 2H, 8.5 Hz), 7.64-7.59 (q, 2H), 6.56-6.52 (d/d, 1H, 7 Hz), 5.58 (s, 1H), 4.60 (m, 2H), 4.49 (m, 2H), 2.30 (s, 3H), 1.90 (s, 3H). $^{13}$C NMR (125 MHz, $CDCl_3$): δ 166.6, 151.5, 135.6, 132.4, 131.3, 129.4, 128.3, 128.1, 127.7, 127.0, 126.6, 125.2, 87.1, 65.9, 63.3.

The general procedure for synthesis of vinyl ether protected calix[4]arenes (calix[4]arenes 1-3) with naphthoylethyl vinyl ether (NCVE) is as follows.

The calix[4]arene (formulas 1-3) (1 mmol) is added to 10 g of dry dioxane. To the solution is added 3-6 equivalents of naphthoylethyl vinyl ether (NCVE) and 1-2 mole % of trifluoroacetic acid (TFA). The mixture is stirred for 2-8 hours at 70° C. The residual acid is neutralized by adding triethylamine and volatiles are removed in vacuo. The resultant vinyl ether-calix[4]arene adducts were separated by reverse-phase column chromatography using acetonitrile/water ($C_{18}$, 80/20 to 100/0 v/v) as eluent.

Molecular glasses with varying number of vinyl ether protecting groups were isolated. It will be appreciated that for any given molecular glass/vinyl ether adduct of a particular molecular weight, there is no precise substitution pattern of the vinyl ether on the core, and that a distribution of different substitutional isomers, each having the same molecular weight, are obtained after isolation. The analytical characterization data based on the molecular weight, for the distribution of substitutional isomers for each adduct is shown in Table 2.

TABLE 2

| Example | Calix[4]arene Core | Equivalents (eq.) of NCVE per eq. of Core | Molecular Weight (m/z) | Tg (° C.) |
| --- | --- | --- | --- | --- |
| Example 1 | 1 | n = 3 | 1872.11 | 78 |
| Example 2 | 1 | n = 4 | 2114.38 | 66 |
| Example 3 | 1 | n = 5 | 2356.65 | 58 |

TABLE 2-continued

| Example | Calix[4]arene Core | Equivalents (eq.) of NCVE per eq. of Core | Molecular Weight (m/z) | Tg (° C.) |
| --- | --- | --- | --- | --- |
| Example 4 | 2 | n = 3 | 1815.97 | — |
| Example 5 | 2 | n = 4 | 2058.26 | 87 |
| Example 6 | 2 | n = 5 | 2300.5 | 76 |
| Example 7 | 3 | n = 3 | 1879.99 | 75 |
| Example 8 | 3 | n = 4 | 2122.26 | 72 |
| Example 9 | 3 | n = 5 | 2364.53 | 66 |

A photoresist polymer, poly(styrene/hydroxystyrene/hydroxystyrene-NCVE/hydroxystyrene-TPSVE-C6); Sty/HS/NCVE/TPSVE-Cy6, 70/10/10/10 molar ratio) was prepared according to the following procedure.

Poly(styrene/hydroxystyrene) copolymer, 70:30 molar ratio (30 g, 0.25 mol; available from Maruzen) was dissolved in dioxolane. The polymer solution was dried azeotropically by distillation. TPSVE-CY6 (16 g, 0.025 mol), trifluoroacetic acid (0.221 g), NCVE (6.05 g, 0.025 mol) were added to the reaction mixture and the contents were heated at 72° C. for 12 hours. The reaction mixture was diluted with tetrahydrofuran (THF) and the reaction mixture was quenched using triethylamine. The reaction mixture was then extracted with ethyl acetate and water (3×100 mL) several times followed by vacuum drying. The resultant polymer was re-dissolved in THF to 12 wt % and precipitated from heptanes/isopropanol (95/5), reprecipitated from heptane, and dried in vacuo to yield 48 g of Sty/HS/NCVE/TPSVE-Cy6 polymer.

The foregoing molecular glasses were formulated into photoresists and evaluated lithographically by EUV exposure.

A positive tone photoresist composition (Resist 1) was prepared by the following procedure. A combination of 0.819 g of the molecular glass compound of Example 1, 0.108 g of a 1 wt % a solution of POLYFOX PF656 surfactant (available from Omnova) in propylene glycol monomethyl ether acetate, 3.0 g of a 1 wt % solution of base additive (TMA-OHBA) in ethyl lactate, 3.0 g of a 5 wt % solution of triphenylsulfonium cyclo(1,3-perfluoropropanedisulfonyl)imide salt in propylene glycol monomethyl ether acetate, 19.51 g of cyclohexanone and 13.59 g of propylene glycol monomethyl ether acetate, were mixed and filtered (0.1 μm filtration).

A positive tone photoresist composition (Resist 2) was prepared by the following procedure. A combination of 0.452 g of the molecular glass compound of Example 1 (the data shown is for example 1), 0.452 g of the photoresist polymer (Sty/HS/NCVE/TPSVE-Cy6, 70/10/10/10 molar ratio), 0.108 g of a 1 wt % a solution of POLYFOX PF656 surfactant (available from Omnova) in propylene glycol monomethyl ether acetate, 2.0 g of a 1 wt % solution of base additive (TMA-OHBA) in ethyl lactate, 1.51 g of a 5 wt % solution of triphenylsulfonium cyclo(1,3-perfluoropropanedisulfonyl) imide salt in propylene glycol monomethyl ether acetate, 19.5 g of cyclohexanone and 16.01 g of propylene glycol monomethyl ether acetate, were mixed and filtered (0.1 μm filtration).

A positive tone photoresist composition (Comparative Resist) was prepared using the following procedure. A positive-tone photoresist composition was prepared by combining in a mixture 0.81 g of a commercially available molecular glass (HSIIA2, available from Idemitsu), 0.10 g of a 1 wt % a solution of POLYFOX PF656 surfactant (available from Omnova) in propylene glycol monomethyl ether acetate, 3.0 g of a 1 wt % solution of base additive (TMA-OHBA) in ethyl lactate, 3.0 g of a 5 wt % solution of triphenylsulfonium cyclo(1,3-perfluoropropanedisulfonyl)imide salt in propylene glycol monomethyl ether acetate, 19.5 g of cyclohexanone and 13.58 g of propylene glycol monomethyl ether acetate solvent.

Each resist was lithographically processed as follows. The photoresist was spun coated using a TEL ACT-8 (Tokyo Electron) coating track or similar equipment onto a 200 mm silicon wafer having an organic underlayer and baked at 90° C. for 60 seconds to form a resist film of about 60 nm in thickness. The resulting photoresist layer was exposed through a patterned mask targeting 28 nm 1:1 line/space features (eMET; EUV radiation, 13.4 nm). The exposed wafers were post exposure baked at 70° C. (Resists 1 and 2) or 100° C. (Comparative Resist) for 60 seconds and developed with 0.26 N aqueous tetramethylammonium hydroxide developer solution to form a positive-tone photoresist pattern.

The exposure doses required to provide a 1:1 resolution are shown for Resists 1 and 2, and for the Comparative Resist (Resist 3) in Table 3. Data for the critical dimension (CD) obtained, and the dose-to-size ($E_{size}$) are shown in the Table. The top down images of the patterned resist are shown in the FIGURE (A-C).

TABLE 3

| Resist | CD (nm) | $E_{size}$ (mJ/cm$^2$) |
|---|---|---|
| Resist 1 | 32 | 35.5 |
| Resist 2 | 28 | 17.4 |
| Comparative Resist (Resist 3) | 32 | 20.0 |

As seen in Table 3, while the same mask was used to image all three resists, however, Resist 1 and Resist 3 (the Comparative Resist) did not resolve 28 nm lines/spaces. It can be seen in the data in Table 3, and in FIG. A-C, that Resist 2 (with a combined molecular glass compound and polymer) has improved photospeed at $E_{size}$ relative to the Comparative Resist, and significantly better $E_{size}$ relative to Resist 1 which only includes a molecular glass compound. However, as seen in the FIGURE, Resist 1 exhibits the cleanest profile. Thus, inclusion of the molecular glass compound in a photoresist can provide both improvements in photospeed and resolution, and cleaner profile, than can use of a photoresist polymer alone.

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A molecular glass compound comprising a vinyl ether adduct of:
   an aromatic vinyl ether of formula $C(R^1)_2=C(R^2)-O-(L)_n-Ar^1$, and
   a calix[4]arene,
   wherein $R^1$ and $R^2$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $Ar^1$ is a halo-containing monocyclic, or substituted or unsubstituted polycyclic or fused polycyclic $C_{6-20}$ aromatic-containing moiety, wherein $R^1$ and $R^2$ are connected to $Ar^1$ when either or both of $R^1$ and $R^2$ is a single bond and n is 0.

2. The molecular glass compound of claim 1, wherein the aromatic vinyl ether is of formula $H_2C=CH-O-(L)_n-Ar^2$, wherein L is a $C_{1-10}$ linking group, n is 0 or 1, and $Ar^2$ is a $C_{6-20}$ aryl, $C_{6-20}$ heteroaryl, $C_{6-20}$ haloaryl, $C_{7-20}$ aralkyl, $C_{7-20}$ heteroaralkyl, or $C_{7-20}$ halo aralkyl.

3. The molecular glass compound of claim 1, wherein L is $-((-CH_2)_m-O-)_p-$, or $-((-CH_2-)_m-O)_p-C(O)-$, and m and p are each independently an integer of 0 to 10.

4. The molecular glass compound of claim 1, wherein the vinyl ether adduct further comprises a cycloaliphatic vinyl ether of the formula $C(R^3)_2=C(R^4)-O-(L)_n-R^5$, wherein $R^3$ and $R^4$ are each independently H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $R^5$ is substituted or unsubstituted and is a $C_{2-30}$ cycloalkyl or $C_{2-40}$ halocycloalkyl.

5. The molecular glass compound of claim 1, wherein the calix[4]arene comprises the tetrameric reaction product of:
   an aromatic compound of formula $C_6R^6_x(OR^7)_y$, wherein $R^6$ is H, F, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, $R^7$ is H, $C_{1-20}$ alkyl, $C_{1-20}$ haloalkyl, x is 6-y and y is 2 or 3, and at least two $OR^7$ groups are meta to one another, and
   an aldehyde of formula $R^8-CHO$, wherein $R^8$ is substituted or unsubstituted and is $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl.

6. The molecular glass compound of claim 5, wherein the aromatic compound is resorcinol, pyrogallol, 3-methoxyphenol, or 3-ethoxyphenol.

7. The molecular glass compound of claim 5, wherein the aldehyde is benzaldehyde, 4-hydroxybenzaldehyde, 2,4-dihydroxybenzaldehyde, 2-hydroxy-4-methoxy benzaldehyde, 3-methoxy-4-hydroxybenzaldehyde, 3-ethoxy-4-hydroxybenzaldehyde, or 3,5-dimethyl-4-hydroxybenzaldehyde.

8. A photoresist composition, comprising the molecular glass compound of claim 1, a solvent, and a photoacid generator.

9. A coated substrate, comprising: (a) a substrate having one or more layers to be patterned on a surface thereof; and (b) a layer of a photoresist composition of claim 8 over the one or more layers to be patterned.

10. A method of forming a molecular glass compound, comprising combining:
   a calix[4]arene, and
   an aromatic vinyl ether of formula $C(R^1)_2=C(R^2)-O-(L)_n-Ar^1$, wherein $R^1$ and $R^2$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $Ar^1$ is a halo-containing monocyclic, or substituted or unsubstituted, polycyclic or fused polycyclic $C_{6-20}$ aromatic-containing ing moiety, wherein $R^1$ and $R^2$ are connected to $Ar^1$ when either or both of $R^1$ and $R^2$ is a single bond and n is 0;

in the presence of an acidic catalyst.

11. A method of forming an electronic device, comprising:
 (a) applying a layer of the photoresist composition of claim 8 on a surface of a substrate to obtain a photoresist composition layer;
 (b) patternwise exposing the photoresist composition layer to activating radiation; and
 (c) developing the exposed photoresist composition layer to provide a resist relief image.

12. The method of claim 11, wherein the activating radiation is e-beam and/or EUV radiation.

* * * * *